United States Patent
Kilinc et al.

(10) Patent No.: US 9,068,937 B2
(45) Date of Patent: Jun. 30, 2015

(54) METHOD AND DEVICE FOR EXAMINING AN EXHAUST GAS SENSOR

(75) Inventors: Muammer Kilinc, Regensburg (DE); Tim Walde, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 251 days.

(21) Appl. No.: 13/059,587

(22) PCT Filed: Aug. 18, 2009

(86) PCT No.: PCT/EP2009/060673
§ 371 (c)(1),
(2), (4) Date: Mar. 9, 2011

(87) PCT Pub. No.: WO2010/020641
PCT Pub. Date: Feb. 25, 2010

(65) Prior Publication Data
US 2011/0146379 A1   Jun. 23, 2011

(30) Foreign Application Priority Data
Aug. 18, 2008   (DE) .......................... 10 2008 038 224

(51) Int. Cl.
G01N 27/419   (2006.01)
G01N 27/417   (2006.01)

(52) U.S. Cl.
CPC ...... *G01N 27/4175* (2013.01); *F01N 2560/026* (2013.01)

(58) Field of Classification Search
CPC ...................... F01N 2560/026; G01N 27/4175
USPC .............. 73/1.06, 23.31–23.33, 28.01–28.06; 204/401, 424–426; 205/783.6, 784, 205/784.5, 785.5
See application file for complete search history.

(56) References Cited

U.S. PATENT DOCUMENTS

| | | | | |
|---|---|---|---|---|
| 5,780,710 A | * | 7/1998 | Murase et al. | ................. 73/1.06 |
| 6,071,393 A | * | 6/2000 | Oshima et al. | ................. 204/425 |

(Continued)

FOREIGN PATENT DOCUMENTS

| | | |
|---|---|---|
| DE | 19956822 | 6/2001 |
| DE | 199 07 947 B4 | 1/2004 |

(Continued)

OTHER PUBLICATIONS

Richard Van Basshuysen, Fred Schäfer; Handbuch Verbrennungsmotor, 2. edition; pp. 589-591; Jun. 2002; ISBN 3-528-13933-1; Friedr. Vieweg & Sohn Verlagsgesellschaft mbH Braunschweig/Wiesbaden Germany (introduction of the Specification).

*Primary Examiner* — Peter Macchiarolo
*Assistant Examiner* — Natalie Huls
(74) *Attorney, Agent, or Firm* — Cozen O'Connor

(57) ABSTRACT

A first voltage (V1) is detected between an auxiliary pump electrode and a reference electrode of an exhaust gas sensor, and a target diagnosis value (SDIAG) is determined as a function of the detected first voltage (V1). A measured current (Im) is detected between a measurement electrode and a second main pump electrode of the exhaust gas sensor, said measured current being set up as the pump current by regulating a second voltage between the measurement electrode and the reference electrode to a pre-defined voltage. An actual diagnosis value (IDIAG) is determined as a function of the detected measured current (Im). An error (ERR) of the exhaust gas sensor is recognized depending on the target diagnosis value (SDIAG) and the actual diagnosis value (IDIAG).

11 Claims, 3 Drawing Sheets

(56) References Cited

U.S. PATENT DOCUMENTS

| | | | |
|---|---|---|---|
| 6,266,993 B1 * | 7/2001 | Diehl et al. | 73/1.06 |
| 6,290,829 B1 | 9/2001 | Kato et al. | |
| 6,300,753 B1 | 10/2001 | Walde et al. | |
| 6,699,383 B2 * | 3/2004 | Lemire et al. | 205/781 |
| 7,427,347 B2 | 9/2008 | Bausewein et al. | |
| 8,398,844 B2 * | 3/2013 | Handler | 205/784.5 |
| 2005/0061684 A1 * | 3/2005 | Bausewein et al. | 205/785.5 |
| 2005/0173264 A1 * | 8/2005 | Reitmeier et al. | 205/783.5 |
| 2005/0284772 A1 * | 12/2005 | Farber | 205/775 |
| 2007/0119708 A1 | 5/2007 | Oya et al. | |
| 2008/0011051 A1 * | 1/2008 | Lemire | 73/23.31 |
| 2009/0223820 A1 * | 9/2009 | Ishiguro et al. | 204/424 |
| 2009/0229978 A1 * | 9/2009 | Mizutani et al. | 204/424 |
| 2009/0242426 A1 * | 10/2009 | Kilinc et al. | 205/781 |
| 2011/0077818 A1 * | 3/2011 | Arlt et al. | 701/34 |

FOREIGN PATENT DOCUMENTS

| | | |
|---|---|---|
| DE | 10 2004 016 986 | 10/2005 |
| DE | 10 2006 053 841 | 5/2008 |
| EP | 1 460 417 | 9/2004 |

* cited by examiner

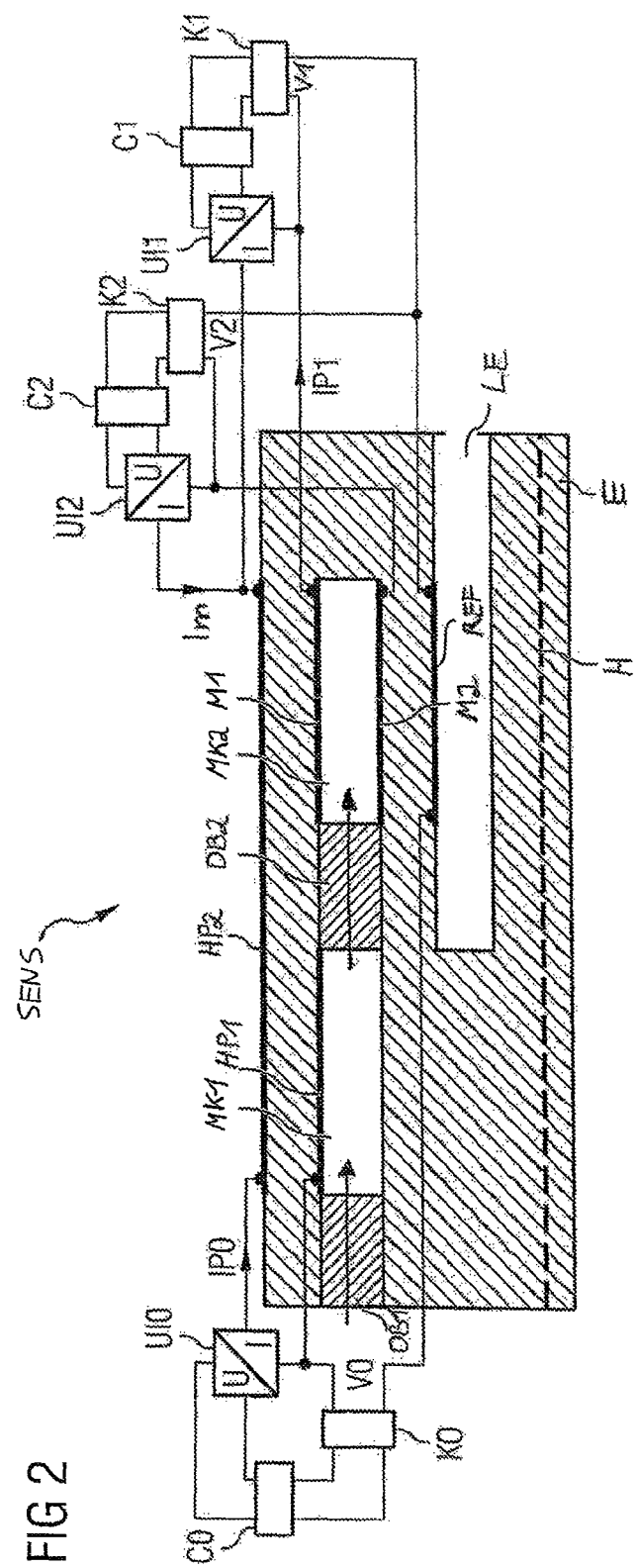

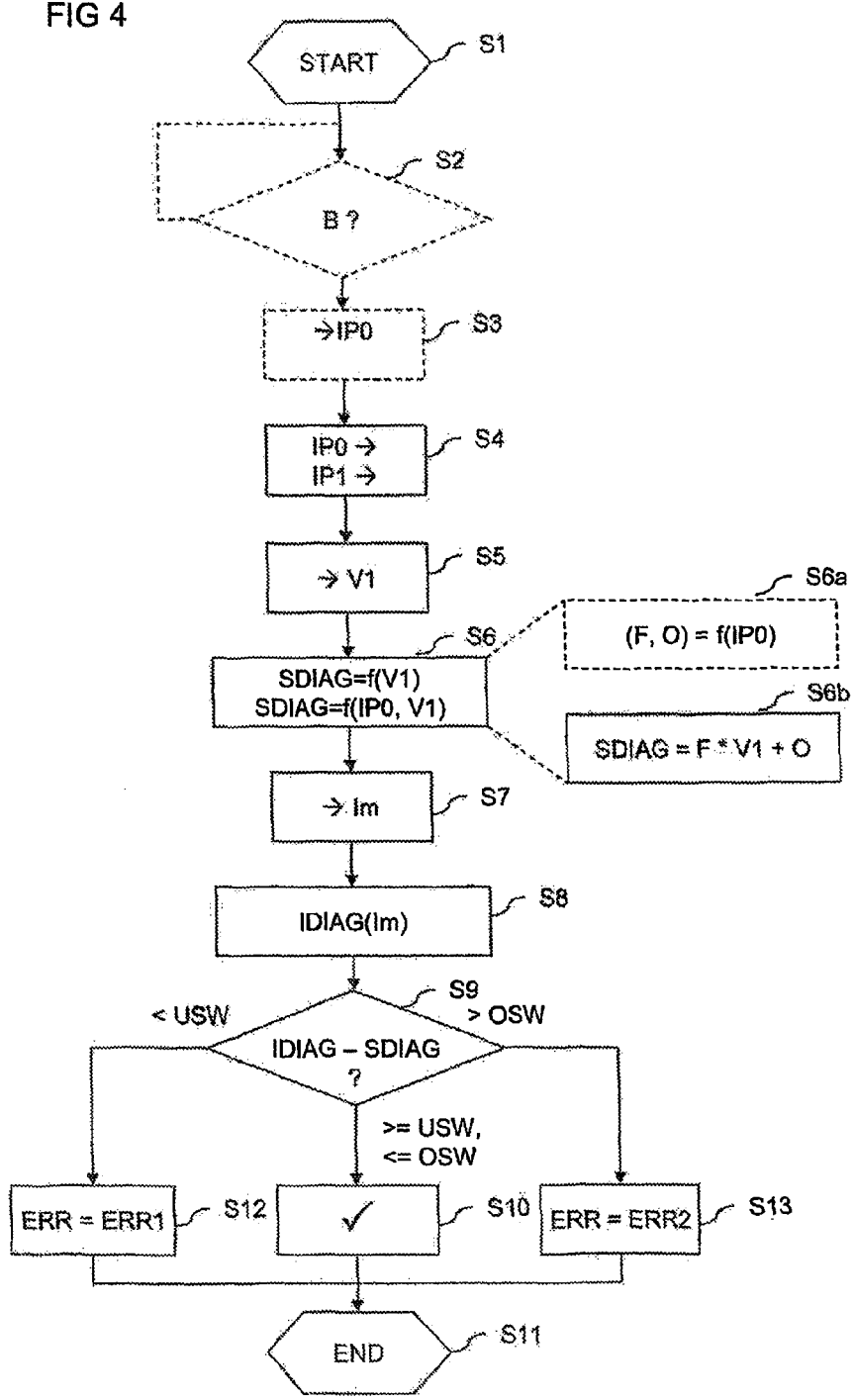

METHOD AND DEVICE FOR EXAMINING AN EXHAUST GAS SENSOR

CROSS REFERENCE TO RELATED APPLICATIONS

This is a U.S. national stage of application No. PCT/EP2009/060673, filed on Aug. 18, 2009. Priority is claimed on German Application No. 10 2008 038 224.8, filed Aug. 18, 2008 the content of which is incorporated here by reference.

BACKGROUND OF THE INVENTION

1. Field of the Invention

The invention relates to a method and to a device for testing an exhaust gas sensor and, in particular, an NOx sensor for motor vehicles with a diesel internal combustion engine.

2. Description of the Prior Art

Due to the increasingly strict legal requirements in terms of permissible emissions of pollutants in motor vehicles in which internal combustion engines are arranged there is a need to keep the emissions of pollutants during operation of the internal combustion engine as low as possible. This can be achieved, for example, by reducing the emissions of pollutants which are produced during the combustion of the air/fuel mixture in the respective cylinder of the internal combustion engine. On the other hand, exhaust gas post-treatment systems are used in internal combustion engines, said exhaust gas post-treatment systems converting the emissions of pollutants which are produced during the combustion process of the air/fuel mixture in the respective cylinder into harmless substances. For this purpose, catalytic converters are used which convert carbon monoxide, hydrocarbons and nitrogen oxides into harmless substances. Both the aimed-at influencing of the production of the emissions of pollutants during the combustion and the conversion of the components of the pollutants with a high degree of efficiency by means of an exhaust gas catalytic converter require a very precisely set air/fuel ratio in the respective cylinder. NOx sensors are used to determine the nitrogen oxide content in the exhaust gas. In this context it is necessary to ensure that the components of the exhaust gas post-treatment system also function in the desired way over a long service life and faults are reliably detected.

The manual "Handbuch Verbrennungsmotor" [Internal Combustion Engine Manual], published by Richard van Basshuysen/Fred Schäfer, $2^{nd}$ Edition, June 2002, Friedrich Vieweg & Sohn Verlagsgesellschaft mbH Braunschweig/Wiesbaden, pages 589 to 590, discloses an NOx sensor based on a $ZrO_2$ ceramic, which NOx sensor has two chambers. In the first chamber, a constant partial pressure of the oxygen contained in the exhaust gas is brought about by applying a pump current. The pump current is inverted proportional to the air/fuel ratio. In the second chamber, the nitrogen oxide contained in the exhaust gas is decomposed by applying a further current. This current is proportional to the nitrogen oxide content in the exhaust gas and forms the measuring signal of the NOx sensor.

Document DE 199 07 947 B4 discloses a circuit for an NOx measuring pickup which has a first measuring cell and a second measuring cell which is connected to the first measuring cell. The measuring cells are located in a solid electrolyte. The circuit has a first circuit arrangement which sets a different oxygen concentration in the first measuring cell than in the gas to be measured by tapping a first Nernst voltage which serves as a first reference variable. A second circuit arrangement sets a different oxygen concentration in the second measuring cell than in the first measuring cell by tapping a second Nernst voltage which serves as a second reference variable. A third circuit arrangement drives a pump current composed of oxygen ions which originate from NOx out of the second measuring cell by tapping a third Nernst voltage which serves as a third reference variable.

The exhaust gas sensor may be contaminated due to components in the exhaust gas. This may make it necessary to carry out diagnostics of the exhaust gas sensor during the ongoing operation of the internal combustion engine.

SUMMARY OF THE INVENTION

The object of the invention is to provide a method and a device for testing an exhaust gas sensor which permit reliable detection of faults in the exhaust gas sensor.

The invention is defined by a method and a corresponding device for testing an exhaust gas sensor. The exhaust gas sensor has a first chamber and a second chamber which are separated from one another by a diffusion barrier. The exhaust gas sensor also has a further diffusion barrier which forms a gas inlet of the first chamber. The first chamber has a first main pump electrode, and the second chamber has a measuring electrode and an auxiliary pump electrode. The exhaust gas sensor also has a second main pump electrode and a reference electrode outside the first and second chambers. A first voltage is sensed between the auxiliary pump electrode and the reference electrode. A set point diagnostic value is determined as a function of the sensed first voltage. A measuring current is sensed between the measuring electrode and the second main pump electrode. The measuring current is set as a pump current by adjusting a second voltage between the measuring electrode and the reference electrode to a predefined voltage. An actual diagnostic value is determined as a function of the sensed measuring current. A fault in the exhaust gas sensor is detected as a function of the set point diagnostic value and the actual diagnostic value.

The advantage is that faults in the exhaust gas sensor, in particular contamination of the exhaust gas sensor and/or detachment of a protective layer from the measuring electrode, can be reliably detected. In addition, the testing of the exhaust gas sensor can advantageously also be reliably carried out in diesel internal combustion engines.

The exhaust gas sensor is embodied, in particular, as an NOx sensor. However, the exhaust gas sensor can likewise be designed to sense one or more other components of the exhaust gas. The first and second voltages are, in particular, Nernst voltages. The first voltage is, in particular, representative of an oxygen content in the second chamber. In particular, for this purpose a predefined first pump current is set between the auxiliary pump electrode and the main pump electrode, and the resulting first voltage is then dependent on the oxygen content in the second chamber.

As a result of the adjustment of the second voltage to the predefined voltage, essentially a stoichiometric gas mixture is formed in the surroundings of the measuring electrode, that is to say the oxygen from the surroundings of the measuring electrode is pumped away by the measuring current in such a way that the surroundings of the measuring electrode are essentially free of oxygen. The predefined voltage is, for example, approximately between 400 and 450 millivolts. However, the predefined voltage can also have a different value.

The testing of the exhaust gas sensor is, in particular, carried out when at least one predefined diagnostic condition applies. The at least one predefined diagnostic condition can, in particular, comprise a predefined operating state, for example overrun conditions, or generally an operating state with an essentially nonvariable load and as a result an essentially nonvariable and predefined oxygen content in the exhaust gas. The at least one predefined diagnostic condition can also comprise, in particular, a low NOx measured value of the exhaust gas sensor which is below a predefined NOx threshold value.

In one advantageous refinement, contamination of the exhaust gas sensor is detected as a fault if an oxygen concentration which is assigned to the actual diagnostic value in the second chamber is lower by at least a predefined first absolute value or factor than an oxygen concentration which is assigned to the set point diagnostic value in the second chamber. In particular, the contamination of the exhaust gas sensor is detected as a fault if the actual diagnostic value is smaller than the set point diagnostic value by at least a predefined lower threshold value. This has the advantage that the contamination of the exhaust gas sensor can be easily and reliably detected.

In a further embodiment, detachment of a protective layer from the measuring electrode is detected as a fault if an oxygen concentration which is assigned to the actual diagnostic value in the second chamber is larger by at least a predefined second absolute value or factor than an oxygen concentration which is assigned to the set point diagnostic value in the second chamber. In particular, the detachment of the protective layer is detected as a fault if the actual diagnostic value is larger than the set point diagnostic value by at least a predefined upper threshold value. This has the advantage that the detachment of the protective layer can be easily and reliably detected.

In a further embodiment, the set point diagnostic value is determined as a function of multiplication of the first voltage by a predefined factor and addition of a predefined shift value. The predefined factor and the predefined shift value are, in particular, predefined individually for the exhaust gas sensor or for a type or a design of the exhaust gas sensor and are determined, for example, as a function of calibration of the exhaust gas sensor, which calibration is carried out, in particular, at the premises of a manufacturer of the exhaust gas sensor within the scope of the manufacture of the exhaust gas sensor. The advantage is that this is easy. In addition, the set point diagnostic value can be determined reliably in this way.

In a further embodiment, a further pump current is sensed between the first main pump electrode and the second main pump electrode. The set point diagnostic value is determined as a function of the sensed further pump current. The advantage is that the set point diagnostic value can be particularly reliably determined in this way. In addition, the testing of the exhaust gas sensor can be carried out even if the current oxygen content in the exhaust gas is unknown. The testing of the exhaust gas sensor can therefore be reliably carried out at different respective prevailing exhaust gas lambda values and can be carried out, in particular, at all prevailing exhaust gas lambda values. As a result, the testing of the exhaust gas sensor is also particularly suitable for diesel internal combustion engines in which exhaust gas lambda values can differ significantly from one, and under certain circumstances fluctuate to a high degree. The further pump current is preferably representative of an oxygen concentration in the exhaust gas and is, in particular, proportional to the oxygen concentration in the exhaust gas.

In this context it is advantageous if the set point diagnostic value is determined as a function of multiplication of the first voltage by a predefined factor and addition of a predefined shift value. The predefined factor and/or the predefined shift value are selected as a function of the sensed further pump current. The predefined factor and the predefined shift value are, in particular, predefined individually for the exhaust gas sensor or for a type or a design of the exhaust gas sensor, for a respectively associated value or value range of the further voltage. The predefined factor, the predefined shift value and/or the respectively associated value or value range of the further pump current are determined, for example, as a function of calibration of the exhaust gas sensor. The calibration is carried out, for example, at the premises of a manufacturer of the exhaust gas sensor within the scope of the manufacture of the exhaust gas sensor. The advantage is that this is very easy and the diagnosis of the exhaust gas sensor can be carried out reliably in this way. The set point diagnostic value can be determined particularly reliably.

BRIEF DESCRIPTION OF THE DRAWINGS

Exemplary embodiments of the invention are explained below with reference to the schematic drawings, in which:

FIG. 2 shows a cross section through an exhaust gas sensor and a measuring circuit, FIG. 4 shows a flowchart.

Elements with the same design or function are provided with the same reference symbols in all the figures.

DETAILED DESCRIPTION OF THE PREFERRED EMBODIMENTS

Figure 1:
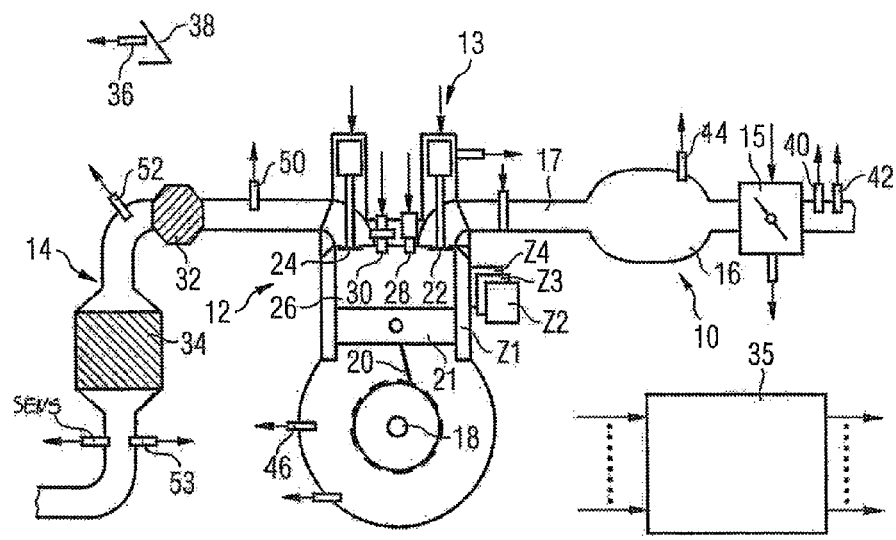
FIG. 1 shows an internal combustion engine with a control device.

FIG. 1 shows an internal combustion engine having an intake section 10, an engine block 12, a cylinder head 13 and an exhaust section 14. The intake section 10 preferably comprises a throttle valve 15, a collector 16 and an intake manifold 17. The intake manifold 17 is extended to a cylinder Z1 in the inlet duct into a combustion chamber 26 of the engine block 12. The engine block 12 comprises a crankshaft 18 which is coupled via a connecting rod 20 to a piston 21 of the cylinder Z1.

The cylinder head 13 comprises a valve drive with a gas inlet valve 22 and a gas outlet valve 24. The cylinder head 13 also comprises an injection valve 28, and a spark plug 30 if the internal combustion engine is embodied, for example, as a petrol internal combustion engine. Alternatively, the injection valve 28 can also be arranged in the intake manifold 17.

An exhaust gas catalytic converter 32 is arranged in the exhaust section 14. In addition, a catalytic converter 34 for reducing NOx is arranged in the exhaust section.

The internal combustion engine is also assigned a control device 35 which is assigned sensors which sense various measurement variables and respectively determine the value of the measurement variables. The control device 35 is designed to determine manipulated variables as a function of at least one of the measurement variables, which manipulated variables can then be converted into one or more actuating signals for controlling actuator elements by means of corresponding actuator drives. The control device 35 can also be embodied as a device for testing an exhaust gas sensor SENS or comprise such a device.

The actuator elements are, for example, the throttle valve 15, the gas inlet valve 22 and gas outlet valve 24, the injection valve 28 or the spark plug 30.

The sensors comprise, for example, a pedal position sensor 36 which senses a position of an accelerator pedal 38. Furthermore, the internal combustion engine has an air mass flow rate sensor 40 which is arranged upstream of the throttle valve 15 and senses an air mass flow there. A temperature sensor 42 upstream of the throttle valve 15 senses an intake air temperature. An intake manifold pressure sensor 44 downstream of the throttle valve 15 is arranged in the collector 16 and senses an intake manifold pressure in the collector 16. Furthermore, the internal compression engine comprises a crankshaft angle sensor 46 which senses a crankshaft angle to which a rotational speed of the internal combustion engine can be assigned.

An exhaust gas probe 50 is arranged upstream of the exhaust gas catalytic converter 32, which exhaust gas probe 50 senses a residual oxygen content of the exhaust gas and the measurement signal of said exhaust gas probe 50 is characteristic of the air/fuel ratio in the combustion chamber 26 of the cylinder Z1 and upstream of the exhaust gas probe 50 before oxidation of the fuel. In addition, a lambda probe 52 is provided which is arranged downstream of the exhaust gas catalytic converter 32 and which senses a residual oxygen content of the exhaust gas and the measurement signal of said lambda probe 52 is characteristic of the air/fuel ratio in the combustion chamber 26 of the cylinder Z1 and upstream of the lambda probe 52.

The exhaust gas probe 50 and the lambda probe 52 are preferably binary lambda probes. The exhaust gas probe 50 and/or the lambda probe 52 can, however, basically be embodied individually or else together as linear lambda probes.

An exhaust gas probe 53 and the exhaust gas sensor SENS are arranged downstream of the exhaust gas catalytic converter 32. The exhaust gas probe 53 senses a residual oxygen content of the exhaust gas and the measurement signal of said exhaust gas probe 53 is characteristic of the air/fuel ratio upstream of the exhaust gas probe 53. The exhaust gas sensor SENS senses, in particular, an NOx concentration of the exhaust gas upstream of the exhaust gas probe 53. In the text which follows, the exhaust gas sensor SENS and a diagnostic method are illustrated with respect to NOx by way of example. However, it is correspondingly also possible for one or more other components of the exhaust gas to be sensed by means of the exhaust gas sensor, and diagnostics can be performed on the exhaust gas sensor SENS with respect to this component or these components.

The exhaust gas sensors SENS preferably comprises the exhaust gas probe 53. This has the disadvantage that just a single sensor has to be made available for sensing the NOx concentration and the residual oxygen content of the exhaust gas. The exhaust gas sensor SENS is preferably designed to output a binary lambda signal. This is advantageous since the binary lambda signal is very sensitive to the residual oxygen content of the exhaust gas. However, the exhaust gas sensor SENS can basically comprise a linear lambda probe.

Depending on the embodiment of the invention, any desired subset of the specified sensors may be present, or additional sensors may also be present.

In addition to the cylinder Z1, further cylinders Z2, Z3, Z4 are preferably also provided, corresponding actuator elements and, if appropriate sensors, being likewise assigned to said cylinders.

The internal combustion engine is preferably embodied as a diesel internal combustion engine. However, the internal combustion engine can also be embodied in a different way, for example as a petrol internal combustion engine.

The device for testing the exhaust gas sensor SENS is preferably arranged in the exhaust gas sensor SENS itself. A system comprising the exhaust gas sensor SENS and the device for testing the exhaust gas sensor SENS can be of such particularly compact design, and can, in particular be independent of the control device 35 of the internal combustion engine.

FIG. 2 shows the exhaust gas sensor SENS in a cross section and a measuring circuit for operating the exhaust gas sensor SENS. The exhaust gas sensor SENS comprises a solid electrolyte E, which is preferably formed from zirconium dioxide $ZrO_2$, and in which a heater H is arranged. An air duct with an air inlet LE for feeding in air from the surroundings is formed in the solid electrolyte E. In addition, a first chamber MK1 and a second chamber MK2 are formed in the solid electrolyte E. The first chamber MK1 comprises a first main pump electrode HP1. The second chamber MK2 comprises an auxiliary pump electrode M1 and a measuring electrode M2. In addition, a second main pump electrode HP2 is arranged on the outside of the solid electrolyte E, and a reference electrode REF is arranged in the air duct. The first chamber MK1 and the second chamber MK2 are separated from one another by a diffusion barrier DB2. A further diffusion barrier DB1 forms a gas inlet for a gas whose NOx content is to be determined. The gas is formed, in particular, by exhaust gas of the internal combustion engine. The diffusion barrier DB2 and the further diffusion barrier DB1 are, in particular, permeable to nitrogen oxides NOx. In general, the diffusion barrier DB2 and the further diffusion barrier DB1 are also permeable to oxygen and/or other components of the gas, and are, in particular, permeable to the exhaust gas of the internal combustion engine.

The measuring circuit comprises a first regulator C1, a first voltage-controlled power source UI1 and preferably a first conditioning device K1. The auxiliary pump electrode M1 and the reference electrode REF of the exhaust gas sensor SENS are coupled to an input of the first regulator C1 via the first conditioning device K1 for the purpose of sensing a first voltage V1 between the auxiliary pump electrode M1 and the reference electrode REF. On the output side, the first regulator C1 is coupled via the first voltage-controlled power source UI1 to the second main pump electrode HP2 and to the auxiliary pump electrode M1 for the purpose of driving a first pump current IP1 between the second main pump electrode HP2 and the auxiliary pump electrode M1. The first regulator C1 is, in particular, designed to regulate the first pump current IP1 as a function of the first voltage V1. The first regulator C1 is also preferably embodied in such a way that during the testing of the exhaust gas sensor SENS the first pump current IP1 is set or adjusted to a predefined pump current which is, in particular, predefined as a constant.

The measuring circuit also comprises a second regulator C2, a second voltage-controlled power source UI2 and preferably a second conditioning device K2. The measuring electrode M2 and the reference electrode REF of the exhaust gas sensor SENS are coupled to an input of the second regulator C2 via the second conditioning device K2 for the purpose of sensing a second voltage V2 between the measuring electrode M2 and the reference electrode REF. On the output side, the second regulator C2 is coupled via the second voltage-controlled power source UI2 to the second main pump electrode HP2 and to the measuring electrode M2 for the purpose of driving a second pump current which forms a measuring current Im, between the second main pump electrode HP2 and the measuring electrode M2. The second regulator C2 is, in particular, designed to regulate the second pump current, that is to say the measuring current Im, as a function of the second voltage V2. The second regulator C2 is, in particular, designed to regulate the measuring current Im in such a way that the second voltage V2 corresponds to a predefined voltage. The predefined voltage is, in particular, predefined in such a way that a stoichiometric gas mixture is formed in the surroundings of the measuring electrode M2, that is to say the surroundings of the measuring electrode M2 are essentially free of oxygen. The predefined voltage can be, for example, approximately between 400 and 450 millivolts. However, the predefined voltage can also be higher than 450 millivolts or lower than 400 millivolts.

In addition, the measuring circuit comprises a further regulator C0, a further voltage controlled power source UI0 and preferably a further conditioning device K0. The first main pump electrode HP1 and the reference electrode REF of the exhaust gas sensor SENS are coupled via the further conditioning device K0 to an input of the further regulator C0 for the purpose of sensing a further voltage V0 between the first main pump electrode HP1 and the reference electrode REF. On the output side, the further regulator C0 is coupled via the further voltage-controlled power source UI0 to the first and second main pump electrodes HP1, HP2 for the purpose of driving a further pump current IP0 between the first and second main pump electrodes HP1, HP2. The further regulator C0 is, in particular, designed to regulate the further pump current IP0 as a function of the further voltage V0. The first chamber MK1 forms, together with the first and second main pump electrodes HP1, HP2 and the reference electrode REF, in particular a binary lambda probe and can represent, in particular, the exhaust gas probe 53.

The pump currents, that is to say the first, second and further pump currents IP1, IP0, cause oxygen to be transported through the solid electrolyte E and into the respective chamber or out of the respective chamber, said solid electrolyte E being heated to a suitable temperature for this by the heater H. The voltages, that is to say the first, second and further voltages V1, V2, V0 are, in particular, Nernst voltages and are dependent on the respective oxygen concentrations in the first chamber MK1, the second chamber MK2 and the surrounding air at the reference electrode REF. In order to test the exhaust gas sensor SENS, the first and further pump currents IP1, IP0 are preferably set or adjusted in such a way that a predefined oxygen concentration, which is in particular, greater than zero parts per million, occurs in the second chamber MK2. The oxygen which is located in the second chamber MK2 acts on the first voltage V1, and, in the case of a sufficiently functionally capable exhaust gas sensor SENS, said oxygen acts on the second pump current, that is to say the measuring current Im.

For example, the measuring electrode M2 is provided with a protective layer which is permeable to nitrogen oxides NOx and oxygen. However, contamination of the measuring electrode M2 and, in particular, of the protective layer may adversely affect the sensitivity of the measuring electrode M2 to oxygen or the permeability of the protective layer to oxygen. The contamination of the exhaust gas sensor SENS causes the measuring current Im to generally deviate from the measuring current Im which is expected for the fault-free exhaust gas sensor SENS. The measuring current Im of the contaminated exhaust gas sensor SENS is, in particular, too low.

However, the protective layer may, for example, become detached from the measuring electrode M2. As a result, it is generally possible for more oxygen to arrive at the measuring electrode M2 than when the protective layer is intact. As a result of the detachment of the protective layer from the measuring electrode M2, the measuring current Im generally deviates from the measuring current Im which is expected for the fault-free exhaust gas sensor SENS. The measuring current Im is in particular too large when the protective layer is detached.

Figure 3:
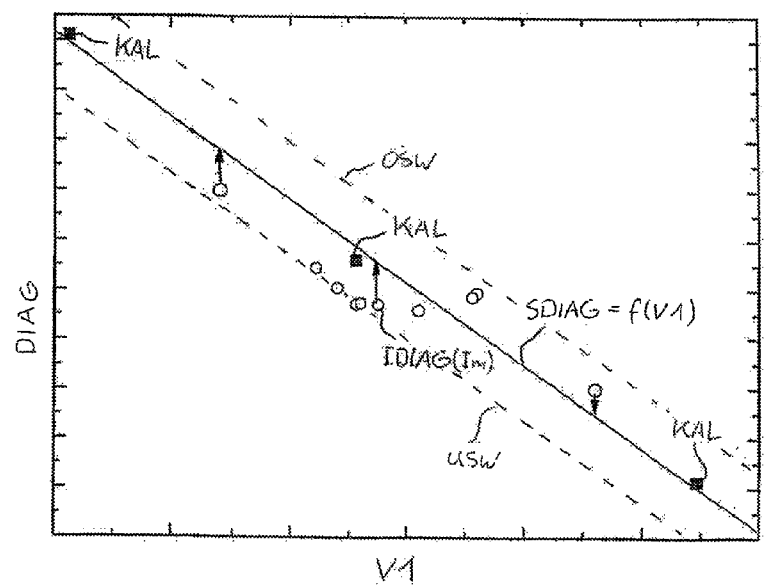
FIG. 3 shows a diagram with diagnostic values which are plotted against a first voltage.

In order to carry out the diagnostics, that is to say the testing of the exhaust gas sensor SENS, a program can be stored in a program memory of the control device 35 and run while the internal combustion engine is operating. FIG. 4 shows a flow chart of a method for testing the exhaust gas sensor SENS and the program. FIG. 3 shows a diagram with diagnostic values DIAG.

The method starts at a step S1. A step S2 can be provided for testing whether at least one predefined diagnostic condition B applies. The at least one predefined diagnostic condition B can comprise, in particular, a predefined operating state of the internal combustion engine, for example overrun conditions, or generally an operating state with an essentially nonvariable load and as a result an essentially nonvariable and predefined oxygen concentration in the exhaust gas. The at least one predefined diagnostic condition can also comprise, in particular, a small NOx measured value of the exhaust gas sensor SENS which is below a predefined NOx threshold value. The predefined NOx threshold value can, for example, be approximately 50 parts per million. However, the predefined NOx threshold value can likewise be higher or lower than 50 parts per million. It is also possible for further or other diagnostic conditions B to be provided. Preferably, the predefined operational state lasts for the duration of the diagnostics performed on the exhaust gas sensor SENS. The duration is, for example, approximately five seconds but can also be longer or shorter.

A step S3 can be provided in which the further pump current IP0 is sensed. The further pump current IP0 is dependent on the oxygen concentration in the first chamber MK1 and is preferably representative of the oxygen concentration in the first chamber MK1. The further pump current IP0 is preferably sensed at the start of the diagnostics. The further pump current IP0 can, in particular, also represent an oxygen concentration of the exhaust gas. It is possible to provide for this purpose that the further voltage V0 be adjusted to a predefined value. The step S3 can, in particular, be dispensed with if the testing of the exhaust gas sensor SENS is carried out in an operating state of the internal combustion engine for which the oxygen concentration in the exhaust gas is known. This can, for example, be the case during overrun conditions.

In a step S4, the first pump current IP1 and the further pump current IP0 are predefined. The first pump current IP1 is preferably predefined reduced in absolute value compared to a normal sensor operating mode of the exhaust gas sensor SENS outside the diagnostics. In a step S5, the first voltage V1 which is set is sensed. The first voltage V1 is dependent on the oxygen concentration in the second chamber MK2 and is preferably representative of the oxygen concentration in the second chamber MK2. The associated oxygen concentration in the second chamber MK2 is preferably assigned to the sensed first voltage V1.

In general, the oxygen concentration, which can be determined as a function of the first voltage V1, is only a rough approximation compared to the oxygen concentration which can in principle be determined as a function of the measuring current Im. However, said oxygen concentration is insensitive to contamination and detachment of the protective layer of the measuring electrode M2.

In a step S6, a set point diagnostic value SDIAG is determined as a function of the first voltage V1. If the further pump current IP0 has been sensed in the step S3, in the step S6 the set point diagnostic value SDIAG is preferably determined as a function of the first voltage V1 and the further pump current IP0 which was sensed in step S3. For example, in a step S6a a predefined factor F and/or a predefined shift value O are selected as a function of the further pump current IP0. The respectively associated predefined factor F and/or predefined shift value O, from which a selection can be made as a function of the further pump current IP0 sensed in the step S3, are preferably predefined and stored for various values or value ranges of the further pump current IP0. If the further pump current IP0 has not been sensed, the predefined factor F and the predefined shift value are preferably permanently predefined independently of the further pump current IP0, being predefined in particular as constants. In a step S6b, the set point diagnostic value SDIAG is determined, for example, as a function of the predefined factor F, the first voltage V1 and the predefined shift value O, for example as a function of multiplication of the predefined factor F by the first voltage V1 and addition of the predefined shift value O: SDIAG=f (F*V1+O), and in particular: SDIAG=F*V1+O.

In FIG. 3, the set point diagnostic value SDIAG is represented as a function of the first voltage V1 as a characteristic curve which is, in particular, a straight line. The predefined factor F and the predefined shift value O are preferably determined experimentally and in particular by calibration. FIG. 3 illustrates, by way of example, three calibration values KAL, which have been sensed, for example, during the calibration of the exhaust gas sensor SENS. The calibration is preferably carried out in a new state of the exhaust gas sensor SENS and is preferably carried out within the scope of the manufacture of the exhaust gas sensor SENS. The characteristic curve results, for example, as a regression straight line as a function of the calibration values KAL, on which straight line the predefined factor F can be determined easily as a function of the gradient thereof, and the predefined shift value O can easily be determined. The calibration values KAL which each form the basis for such a characteristic curve are preferably sensed for a predefined oxygen concentration in a gas which is used for the calibration, if appropriate instead of the exhaust gas of the internal combustion engine. By varying the predefined oxygen concentration in the gas it is possible for various characteristic curves with different predefined factors F and/or predefined shift values O to be formed between which, according to step S6a, it is possible to select as a function of the further pump current IP0. In this way a high degree of accuracy of the set point diagnostic value SDIAG is possible.

In a step S7, the measuring current Im is sensed. In a step S8, an actual diagnostic value IDIAG which is associated with the measuring current Im is determined. An associated oxygen concentration at the measuring electrode M2 in the second chamber MK2 which, however, under certain circumstances, does not correspond to the actual oxygen concentration owing, for example, to contamination or detachment of the protective layer, is preferably assigned to the measuring current Im or the diagnostic value IDIAG. In a step S9, it is tested whether deviation of the oxygen concentration assigned to the actual diagnostic value IDIAG from the oxygen concentration assigned to the set point diagnostic value SDIAG occurs, by testing, for example, whether a deviation of the actual diagnostic value IDIAG from the set point diagnostic value SDIAG exceeds a predefined threshold value. If this is not the case, the exhaust gas sensor SENS is detected in a step S10 as free of faults and the testing of the exhaust gas sensor SENS is ended in a step S11.

However, if it is detected in the step S9, for example, that the actual diagnostic value, IDIAG is lower than the set point diagnostic value SDIAG by more than a predefined lower threshold value USW, that is to say that the oxygen concentration which is assigned to the actual diagnostic value IDIAG is too low compared to the oxygen concentration assigned to the set point diagnostic value SDIAG, in a step S12 a first fault ERR1 is detected as a fault ERR of the exhaust gas sensor SENS. The first fault ERR1 corresponds, in particular, to the contamination of the exhaust gas sensors SENS. If appropriate, a corresponding entry is made in a fault memory and/or the fault ERR is signaled. The testing of the exhaust gas sensor SENS is ended in the step S11.

If it is detected in the step S9 that, for example, the actual diagnostic value IDIAG is higher than the set point diagnostic value SDIAG by more than a predefined upper threshold value OSW, that is to say that the oxygen concentration assigned to the actual diagnostic value IDIAG is too high compared to the oxygen concentration assigned to the set point diagnostic value SDIAG, in a step S13 a second fault ERR2 is detected as a fault ERR of the exhaust gas sensor SENS. The first fault ERR2 corresponds, in particular, to the detachment of the protective layer from the measuring electrode M2 of the exhaust gas sensor SENS. If appropriate, a corresponding entry is made in the fault memory and/or the fault ERR is signaled. The testing of the exhaust gas sensor SENS is ended in the step S11.

The relationship between diagnostic values DIAG and the assigned oxygen concentration can alternatively also be predefined inversely, that is to say, for example, the first fault ERR1 is detected if it is detected in the step S9 that the actual diagnostic value IDIAG is higher than the set point diagnostic value SDIAG by more than the predefined lower threshold value USW, which means that the oxygen concentration assigned to the actual diagnostic value IDIAG is too low compared to the oxygen concentration assigned to the set point diagnostic value SDIAG, and, for example, the second fault ERR2 is detected if it is detected in the step S9 that the actual diagnostic value IDIAG is lower than the set point diagnostic value SDIAG by more than the predefined upper threshold value OSW, which means that the oxygen concentration assigned to the actual diagnostic value IDIAG is too high compared to the oxygen concentration assigned to the set point diagnostic value SDIAG.

The invention claimed is:

1. A method for testing an exhaust gas sensor having a first chamber, a second chamber, a first diffusion barrier separating the first and second chambers, and a second diffusion barrier forming a gas inlet of the first chamber, the first chamber having first main pump electrode, the second chamber having a measuring electrode and an auxiliary pump electrode, and a second main pump electrode and a reference electrode being disposed outside of the first and second chambers, said method comprising:
   sensing a first voltage as a predefined voltage between the auxiliary pump electrode and the reference electrode;
   determining a set point diagnostic value as a function of the sensed first voltage multiplied by a predefined factor and adding a predefined shift value to the resulting value, wherein the predefined shift value is determined as a function of a calibration of the exhaust gas sensor;
   sensing a measuring current between the measuring electrode and the second main pump electrode, the measuring current being set as a pump current by adjusting a second voltage between the measuring electrode and the reference electrode to the predefined voltage, and determining an actual diagnostic value as a function of the sensed measuring current; and
   detecting a fault in the exhaust gas sensor as a function of the set point diagnostic value and the actual diagnostic value.

2. The method of claim 1, wherein the detecting a fault comprises detecting contamination of the exhaust gas sensor as the fault if an oxygen concentration assigned to the actual diagnostic value in the second chamber is lower by at least a predefined first absolute value or factor than an oxygen concentration assigned to the set point diagnostic value in the second chamber.

3. The method of claim 1, wherein the detecting a fault comprises detecting detachment of a protective layer from the measuring electrode as the fault if an oxygen concentration assigned to the actual diagnostic value in the second chamber is larger by at least a predefined second absolute value or factor than an oxygen concentration assigned to the set point diagnostic value in the second chamber.

4. The method of claim 1, further comprising sensing a further pump current between the first main pump electrode and the second main pump electrode, wherein the set point diagnostic value is determined as a function of the sensed further pump current.

5. The method of claim 4, wherein at least one of the predefined factor and the predefined shift value are selected as a function of the sensed further pump current.

6. The method of claim 1, wherein the predefined voltage is a constant voltage.

7. The method of claim 6, wherein the set point diagnostic value and the actual diagnostic value are related to current at the constant voltage.

8. A device for testing an exhaust gas sensor, the exhaust gas sensor having
a first chamber,
a second chamber,
a first diffusion barrier separating the first and second chambers, and
a second diffusion barrier forming a gas inlet of the first chamber,
the first chamber having a first main pump electrode and the second chamber has a measuring electrode and an auxiliary pump electrode, and
a second main electrode and a reference electrode being disposed outside of the first and second chambers,
the device being configured to:
sense a first voltage as a predefined voltage between the auxiliary pump electrode and the reference electrode and
determine a set point diagnostic value as a function of the sensed first voltage multiplied by a predefined factor and the resulting value being added to a predefined shift value, wherein the predefined shift value is determined as a function of a calibration of the exhaust gas sensor,
sense a measuring current between the measuring electrode and the second main pump electrode, the measuring current being set as a pump current by adjusting a second voltage between the measuring electrode and the reference electrode to the predefined voltage, and
determine an actual diagnostic value as a function of the sensed measuring current, and detect a fault in the exhaust gas sensor as a function of the set point diagnostic value and the actual diagnostic value.

9. The device of claim 8, wherein the predefined voltage is a constant voltage.

10. The device of claim 9, wherein the set point diagnostic value and the actual diagnostic value are related to current at the constant voltage.

11. A method for testing an exhaust gas sensor having a first chamber, a second chamber, a first diffusion barrier separating the first and second chambers, and a second diffusion barrier forming a gas inlet of the first chamber, the first chamber having first main pump electrode, the second chamber having a measuring electrode and an auxiliary pump electrode, and a second main pump electrode and a reference electrode being disposed outside of the first and second chambers, said method comprising:

sensing a first voltage as a predefined voltage between the auxiliary pump electrode and the reference electrode;

determining a set point diagnostic value based at least in part on a first current between the measuring electrode and the second main pump electrode at the first voltage;

sensing a measuring current between the measuring electrode and the second main pump electrode, the measuring current being set as a pump current by adjusting a second voltage between the measuring electrode and the reference electrode to the predefined voltage;

determining an actual diagnostic value as a function of the sensed measuring current; and detecting a fault in the exhaust gas sensor as a function of the set point diagnostic value and the actual diagnostic value.

* * * * *